US012288603B2

(12) United States Patent
May et al.

(10) Patent No.: US 12,288,603 B2
(45) Date of Patent: Apr. 29, 2025

(54) MACHINE-LEARNING BASED EFFICACY PREDICTIONS BASED ON GENETIC AND BIOMETRIC INFORMATION

(71) Applicant: ENDOCANNA HEALTH, INC., Burbank, CA (US)

(72) Inventors: Len May, Studio City, CA (US); Eric Kaufman, Sherman Oaks, CA (US)

(73) Assignee: Endocanna Health, Inc., Burbank, CA (US)

( * ) Notice: Subject to any disclaimer, the term of this patent is extended or adjusted under 35 U.S.C. 154(b) by 259 days.

(21) Appl. No.: 17/717,939

(22) Filed: Apr. 11, 2022

(65) Prior Publication Data

US 2022/0328155 A1 Oct. 13, 2022

Related U.S. Application Data

(60) Provisional application No. 63/173,096, filed on Apr. 9, 2021.

(51) Int. Cl.
*G16H 20/10* (2018.01)
*G16B 20/40* (2019.01)
(Continued)

(52) U.S. Cl.
CPC ............ *G16H 20/10* (2018.01); *G16B 20/40* (2019.02); *G16B 40/00* (2019.02); *G16H 10/60* (2018.01); *G16H 40/67* (2018.01); *G16H 50/20* (2018.01)

(58) Field of Classification Search
CPC ........ G16H 20/10; G16H 40/67; G16H 10/60; G16H 50/20; G16B 40/00; G16B 20/40
See application file for complete search history.

(56) References Cited

U.S. PATENT DOCUMENTS 9,008,415 B2 * 4/2015 Paris ...................... G06N 20/00
  382/159
9,292,911 B2 * 3/2016 Paris ......................... G06T 5/92
  (Continued)

FOREIGN PATENT DOCUMENTS

WO  WO-2020227440 A1 * 11/2020 ........... A61K 31/352

OTHER PUBLICATIONS

Nanni, 2017, Elsevier, pp. 158-172.*
(Continued)

*Primary Examiner* — Michael I Ezewoko
(74) *Attorney, Agent, or Firm* — McDonnell Boehnen Hulbert & Berghoff LLP

(57) ABSTRACT

Examples disclosed herein may involve a computing system that is configured to (i) identify a cannabinoid formulation for which to model efficacy for a given health condition shared by a plurality of individuals, (ii) receive respective efficacy information indicating the efficacy of the cannabinoid formulation for the plurality of individuals, (iii) receive respective genetic information for the plurality of individuals, (iv) receive respective biometric information for the plurality of individuals, (v) apply machine learning techniques to group the plurality of individuals into one or more groups based on their (a) respective efficacy information and (b) similarities in their respective genetic information and respective biometric information, and (vi) embody the one or more groups into a machine learning model that functions to (a) receive, as input data, information for a given individual and (ii) based on an evaluation of the received input data, output an efficacy prediction for the given individual.

20 Claims, 6 Drawing Sheets

(51) Int. Cl.
  *G16B 40/00* (2019.01)
  *G16H 10/60* (2018.01)
  *G16H 40/67* (2018.01)
  *G16H 50/20* (2018.01)

(56) References Cited

U.S. PATENT DOCUMENTS

| | | | | |
|---|---|---|---|---|
| 9,445,713 | B2* | 9/2016 | Douglas | G06F 18/24 |
| 9,514,248 | B1* | 12/2016 | Guan | H04L 9/40 |
| 9,514,391 | B2* | 12/2016 | Perronnin | G06V 10/82 |
| 9,838,409 | B2* | 12/2017 | Flacher | H04L 63/1425 |
| 10,052,026 | B1* | 8/2018 | Tran | A61B 5/165 |
| 10,182,066 | B2* | 1/2019 | Flacher | H04L 63/1458 |
| 10,218,726 | B2* | 2/2019 | Vasseur | H04L 67/303 |
| 10,445,879 | B1* | 10/2019 | Fuchs | G06V 10/764 |
| 10,553,318 | B2* | 2/2020 | Athey | G16B 20/20 |
| 10,691,751 | B2* | 6/2020 | Atlas | G06F 16/285 |
| 10,810,736 | B2* | 10/2020 | Fuchs | G16H 30/40 |
| 10,957,041 | B2* | 3/2021 | Yip | G06N 3/084 |
| 11,036,964 | B2* | 6/2021 | Srivastava | G06V 10/82 |
| 11,074,495 | B2* | 7/2021 | Zadeh | G06F 18/2413 |
| 11,139,081 | B2* | 10/2021 | Tran | G06Q 30/0206 |
| 11,263,748 | B2* | 3/2022 | Yip | G06N 3/045 |
| 11,348,239 | B2* | 5/2022 | Yip | G06V 20/698 |
| 11,348,240 | B2* | 5/2022 | Yip | G06N 3/045 |
| 11,348,661 | B2* | 5/2022 | Yip | G06N 3/045 |
| 11,423,086 | B2* | 8/2022 | Atlas | H04L 67/535 |
| 11,448,727 | B2* | 9/2022 | Ozturk | G01S 7/354 |
| 11,461,690 | B2* | 10/2022 | Szeto | G06N 20/10 |
| 11,501,429 | B2* | 11/2022 | Stamatoyannopoulos | G16B 20/00 |
| 11,527,323 | B2* | 12/2022 | Michuda | G16B 30/00 |
| 11,538,155 | B2* | 12/2022 | Fuchs | G06V 10/7635 |
| 11,610,307 | B2* | 3/2023 | Yip | G06T 7/0012 |
| 11,681,953 | B2* | 6/2023 | Drake | G16B 40/20 705/3 |
| 11,682,098 | B2* | 6/2023 | Yip | G06T 7/11 382/133 |
| 11,687,778 | B2* | 6/2023 | Ciftci | G06V 40/40 382/115 |
| 11,694,122 | B2* | 7/2023 | Szeto | G16H 10/60 706/10 |
| 11,704,366 | B2* | 7/2023 | Atlas | G06F 16/285 707/737 |
| 11,705,226 | B2* | 7/2023 | Colley | G16B 40/00 705/3 |
| 11,769,521 | B1* | 9/2023 | Pitzer | G10L 15/16 704/231 |
| 11,810,677 | B2* | 11/2023 | Fuchs | G06F 18/2113 |
| 11,847,532 | B2* | 12/2023 | Drake | G16B 20/00 |
| 11,887,696 | B2* | 1/2024 | Frey | G06N 3/04 |
| 11,900,600 | B2* | 2/2024 | Stamatoyannopoulos | G16B 40/20 |
| 2014/0222349 | A1* | 8/2014 | Higgins | G16B 20/00 702/19 |
| 2016/0250270 | A1 | 9/2016 | Wendschuh et al. | |
| 2016/0307071 | A1* | 10/2016 | Perronnin | G06F 18/214 |
| 2017/0104773 | A1* | 4/2017 | Flacher | H04L 63/1458 |
| 2017/0279829 | A1* | 9/2017 | Vasseur | H04L 63/1458 |
| 2017/0330264 | A1* | 11/2017 | Youssef | G06F 16/24578 |
| 2018/0018590 | A1* | 1/2018 | Szeto | G16H 50/20 |
| 2018/0374567 | A1 | 12/2018 | Toumazou et al. | |
| 2019/0046499 | A1 | 2/2019 | Segreti | |
| 2019/0273509 | A1* | 9/2019 | Elkind | H03M 7/4093 |
| 2019/0273510 | A1* | 9/2019 | Elkind | H03M 7/4093 |
| 2019/0343465 | A1 | 11/2019 | Sipolins et al. | |
| 2020/0211688 | A1* | 7/2020 | Liu | G16H 20/10 |
| 2020/0327962 | A1* | 10/2020 | Chittenden | G16B 40/30 |
| 2021/0065847 | A1* | 3/2021 | Valouev | G16B 40/00 |
| 2021/0069230 | A1 | 3/2021 | Rees et al. | |
| 2021/0098129 | A1 | 4/2021 | Neumann | |
| 2021/0193280 | A1 | 6/2021 | Esmailian et al. | |
| 2021/0229281 | A1* | 7/2021 | Natarajan | B25J 9/1669 |
| 2021/0319907 | A1* | 10/2021 | Harley | G16H 50/70 |
| 2021/0350937 | A1 | 11/2021 | Lefkofsky et al. | |
| 2021/0375406 | A1 | 12/2021 | Neumann | |
| 2022/0164935 | A1* | 5/2022 | Girshick | G06T 5/50 |
| 2022/0262108 | A1* | 8/2022 | Hida | G06N 3/088 |
| 2022/0392637 | A1* | 12/2022 | Kollada | G16H 50/30 |
| 2022/0405644 | A1* | 12/2022 | Szeto | G06N 20/00 |
| 2023/0018537 | A1* | 1/2023 | Brandsma | G16H 50/50 |
| 2023/0083000 | A1* | 3/2023 | Fujimoto | G06V 30/26 382/159 |
| 2023/0170050 | A1* | 6/2023 | Cooper | G16B 40/20 706/21 |
| 2023/0187070 | A1* | 6/2023 | Michuda | G16H 10/40 702/19 |
| 2023/0255564 | A1* | 8/2023 | Pascual-Leone | G16H 40/63 600/301 |
| 2023/0386185 | A1* | 11/2023 | Park | G06V 10/761 |
| 2024/0021324 | A1* | 1/2024 | Fuchs | G06F 18/2431 |
| 2024/0038375 | A1* | 2/2024 | Mohtar | G16H 50/70 |

OTHER PUBLICATIONS

International Searching Authority, PCT International Search Report and Written Opinion, PCT International Application No. PCT/US22/24271, dated Jun. 29, 2022, 10 pages.

* cited by examiner

MACHINE-LEARNING BASED EFFICACY PREDICTIONS BASED ON GENETIC AND BIOMETRIC INFORMATION

CROSS-REFERENCE TO RELATED APPLICATIONS

This application claims the benefit of U.S. Provisional Application No. 63/173,096, filed Apr. 9, 2021, the disclosure of which is explicitly incorporated by reference herein in its entirety.

BACKGROUND

Every individual has an endocannabinoid system comprised of chemical receptors in the brain, immune system, and central nervous system (for example, cannabinoid receptors CB1 and CB2). Medical use of cannabis and associated phytocannabinoids is becoming widely accepted in the United States as an alternative form of medicine. Many states have legalized its use for qualified medical conditions such as chronic pain, epilepsy, sleep disorders, anxiety, cancer, glaucoma, nausea, ALS, Alzheimer's disease, Crohn's disease, Post-traumatic Stress Disorder (PTSD), arthritis, fibromyalgia, and others.

Single nucleotide polymorphisms (SNPs) are stable genetic markers throughout the human genome, which can be tested for their association with various disease traits. These markers can also be associated with various traits that can determine an individual's sensitivity to certain compounds present in cannabis such as cannabinoids, terpenes, nitrogenous compounds, flavonoids, non-cannabinoid phenols and other miscellaneous chemical constituents. These endogenous endocannabinoid SNP markers can be tested in a patient and used as biomarkers that may predict how a patient will react or respond to the metabolism of compounds such as delta-9-THC, cannabidiol, other cannabinoids, and terpenoids found in cannabis. Furthermore, these biomarkers may suggest the best modality of treatment based on an individual's genetic profile and presence of specific enzymes or lack thereof that may result in negative side-effects from these compounds.

SUMMARY

Individuals may send their genetic information to various providers with the hope of learning something about themselves, which may include where their ancestors inhabited the Earth, whether they are susceptible to certain cancers or diseases, or whether they may react positively or negatively to certain compounds when undergoing treatments for a variety of health conditions. Each provider may determine this information by testing particular parts of the individual's genome. These particular parts of the genome are genetic markers referred to as single nucleotide polymorphisms (SNPs). The SNPs can be tested for their association with various disease traits or to determine how an individual will react to particular compounds. For example, if an individual is determined to have heterozygous alleles (C/T) at the rs1049353 polymorphism of the CNR1 gene, the individual may suffer from reduced focus when using cannabis. These genetic markers collectively make up an individual's genotype.

However, in a scenario where an individual seeks to understand whether they will react positively or negatively to a given compound, the individual's genotype alone may not provide the requisite amount of information to make an informed decision. Accordingly, even if an individual's genotype may indicate that they would be more likely to react a certain way to the given compound, other factors beyond genotype may potentially affect the outcome. In this respect, it may be advantageous to look at an individual's phenotype (e.g., how an individual's genes are expressed) to improve an efficacy prediction of the given compound. However, an individual's phenotype may be influenced by a large number of genes, making it unclear which particular gene expression(s) in the individual's phenotype may be responsible for the individual's interaction with the given compound.

Thus, in order to develop more informed predictions of a given individual's reaction to a given compound, one may look at how other individuals with a similar genotype and/or phenotype to the given individual have reacted to the given compound. In order to accomplish this, one would have to (i) analyze each of the other individual's genome, (ii) identify the relevant SNPs for a particular health outcome, (iii) compare and contrast the SNPs of the given individual with the SNPs of the other individuals in order to determine relevant similarities, and (iv) determine the given individual's likely reaction to the given compound based on the similarities and/or differences. However, the amount of information alone that one would need to collect and analyze to make such a determination is very burdensome and time consuming.

Accordingly, the embodiments herein support methods, devices, and systems for modeling the efficacy of a given compound for a health condition shared by a plurality of individuals. These embodiments involve the collection and analysis of genetic information, biometric information, feedback information, and efficacy information from various sources to determine relevant similarities shared by the plurality of individuals. These embodiments also involve using the efficacy model to provide an efficacy prediction for a compound for a given health condition experienced by a given individual.

At a high level, genetic information may take various forms, examples of which include genotypes, haplotypes, genetic variants, copy number variations, phenotypes, polygenic risk scores, genealogy information, and various genetic mutations such as insertions, deletions, missense, nonsense, and frameshift mutations. The genetic information may take other forms as well.

Further, biometric information may take various forms, examples of which include photoplethysmography data, oxygen saturation levels, arterial elasticity, peripheral elasticity, sleep information, glucose levels, and blood pressure. The biometric information may be obtained by one or more biometric devices. The biometric devices may take various forms as well, examples of which include wearable devices (e.g., APPLE WATCH®, FITBIT®, GARMIN®, WHOOP®, etc.) and/or medical professional monitoring devices (e.g., glucose monitors, blood pressure monitors, etc.). The biometric devices may take other forms as well.

Additionally, feedback information may be related to individuals' experience with a given compound and may take various forms, examples of which include survey information (e.g., questionnaires with predefined questions and answers) and interviews conducted in a manner consistent with Real-World Evidence (RWE) accumulation.

In general, efficacy information may take various forms, one example of which includes an indication of whether a given compound was effective for a given individual's health condition (e.g., whether and/or how well a particular cannabinoid achieved the individual's desired effect).

Once the system determines an efficacy prediction of a given compound for the individual, the system may present the individual with the efficacy prediction. The system may present the efficacy prediction in various ways, one example of which may include presenting one or more graphical user interfaces to the individual via a computing device that is accessible by the individual.

In this way, after receiving the efficacy prediction, the individual may be able to confidently choose and begin using the given compound. This may be beneficial as it may speed up or eliminate the need for the individual to self-treat via a prolonged trial-and-error process.

Accordingly, in one aspect, disclosed herein is a method that involves (i) identifying a cannabinoid formulation for which to model efficacy for a given health condition shared by a plurality of individuals, (ii) receiving respective efficacy information indicating the efficacy of the cannabinoid formulation for the plurality of individuals, (iii), receiving respective genetic information for the plurality of individuals, (iv) receiving respective biometric information for the plurality of individuals, (v) applying one or more machine learning techniques to group the plurality of individuals into one or more groups based on their (a) respective efficacy information and (b) similarities in their respective genetic information and respective biometric information, and (vi) embodying the one or more groups into a machine learning model that functions to (a) receive, as input data, given genetic information and given biometric information for a given individual and (b) based on an evaluation of the received input data, output an efficacy prediction, for the given individual, of the cannabinoid formulation for the given health condition.

In some examples, the respective genetic information comprises a genome for each of the plurality of individuals.

In other examples, the respective biometric information comprises one or more of (i) photoplethysmography data, (ii) oxygen saturation levels, (iii) arterial elasticity, (iv) peripheral elasticity, (v) sleep information, (vi) glucose levels, and (vii) blood pressure.

In still other examples, receiving the respective biometric information comprises receiving at least a portion of the biometric information from a biometric device.

In yet other examples, the method further involves receiving respective feedback information for the plurality of individuals, where applying one or more machine learning techniques to group the plurality of individuals into one or more groups is also based on similarities in their respective feedback information.

In some examples, the one or more machine learning techniques comprises a k-nearest neighbor machine learning technique.

In other examples, the one or more machine learning techniques comprises a k-means machine learning technique.

In some examples, the method further involves reducing the dimensionality of the respective genetic information prior to applying the one or more machine learning techniques.

In other examples, the method further involves reducing the dimensionality of the respective biometric information prior to applying the one or more machine learning techniques.

In still other examples, the method further involves reducing the dimensionality of the respective genetic information and the respective biometric information prior to applying the one or more machine learning techniques.

In another aspect, disclosed herein is a method that involves (i) receiving a request to provide an efficacy prediction for a cannabinoid formulation for a given health condition experienced by a given individual, (ii) receiving given genetic information for the given individual, (iii) receiving given biometric information for the given individual, (iv) using a machine learning model that has been trained with respective efficacy information, respective genetic information, and respective biometric information for a plurality of individuals that share the given health condition to derive the efficacy prediction, and (v) providing the efficacy prediction to the given individual.

In some examples, receiving given biometric information for the given individual comprises receiving biometric information from a user device of the given individual.

In other examples, the method further involves receiving given feedback information for the given individual, where the machine learning model has also been trained with respective feedback information for the plurality of individuals.

In another aspect, the disclosed technology may take the form of a computing system comprising at least one processor, a non-transitory computer-readable medium, and program instructions stored on the non-transitory computer-readable medium that are executable by the at least one processor such that the computing system is configured to carry out the functions of the aforementioned methods.

In yet another aspect, the disclosed technology may take the form of a non-transitory computer-readable medium comprising program instructions stored thereon that are executable to cause a computing system to carry out the functions of the aforementioned methods.

These as well as other embodiments, aspects, advantages, and alternatives will become apparent to those of ordinary skill in the art by reading the following detailed description, with reference where appropriate to the accompanying drawings. Further, this summary and other descriptions and figures provided herein are intended to illustrate embodiments by way of example only and, as such, that numerous variations are possible. For instance, structural elements and process steps can be rearranged, combined, distributed, eliminated, or otherwise changed, while remaining within the scope of the embodiments as claimed.

DETAILED DESCRIPTION

Example methods, devices, and systems are described herein. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features unless stated as such. Thus, other embodiments can be utilized and other changes can be made without departing from the scope of the subject matter presented herein. Accordingly, the example embodiments described herein are not meant to be limiting. It will be readily understood that the aspects of the present disclosure, as generally described herein, and illustrated in the figures, can be arranged, substituted, combined, separated, and designed in a wide variety of different configurations. For example, the separation of features into "client" and "server" components may occur in a number of ways.

Further, unless context suggests otherwise, the features illustrated in each of the figures may be used in combination with one another. Thus, the figures should be generally viewed as component aspects of one or more overall embodiments, with the understanding that not all illustrated features are necessary for each embodiment.

Additionally, any enumeration of elements, blocks, or steps in this specification or the claims is for purposes of clarity. Thus, such enumeration should not be interpreted to require or imply that these elements, blocks, or steps adhere to a particular arrangement or are carried out in a particular order.

Regardless of how they may be implemented, the embodiments herein may make use of one or more computing devices. These computing devices may include, for example, client devices under the control of users, and server devices that directly or indirectly interact with the client devices. Such devices are described in the following section.

I. Example Computing Devices and Cloud-Based Computing Environments

Figure 1:
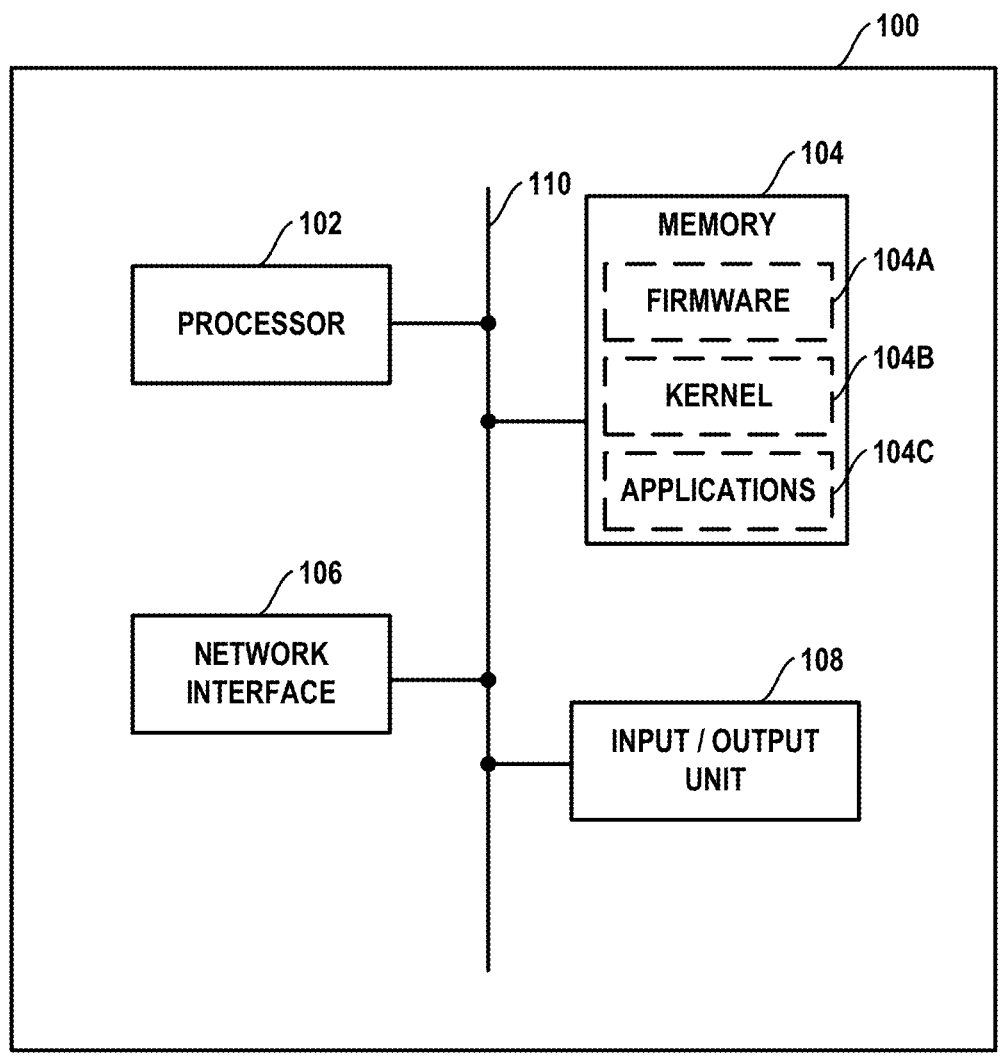
FIG. 1 illustrates a schematic drawing of a computing device, in accordance with example embodiments.

FIG. 1 is a simplified block diagram exemplifying a computing device 100, illustrating some of the components that could be included in a computing device arranged to operate in accordance with the embodiments herein. Computing device 100 could be a client device (e.g., a device actively operated by a user), a server device (e.g., a device that provides computational services to client devices), or some other type of computational platform. Some server devices may operate as client devices from time to time in order to perform particular operations, and some client devices may incorporate server features.

In this example, computing device 100 includes processor 102, memory 104, network interface 106, and an input/output unit 108, all of which may be coupled by a system bus 110 or a similar mechanism. In some embodiments, computing device 100 may include other components and/or peripheral devices (e.g., detachable storage, printers, and so on).

Processor 102 may be one or more of any type of computer processing element, such as a central processing unit (CPU), a co-processor (e.g., a mathematics, graphics, or encryption co-processor), a digital signal processor (DSP), a network processor, and/or a form of integrated circuit or controller that performs processor operations. In some cases, processor 102 may be one or more single-core processors. In other cases, processor 102 may be one or more multi-core processors with multiple independent processing units. Processor 102 may also include register memory for temporarily storing instructions being executed and related data, as well as cache memory for temporarily storing recently-used instructions and data.

Memory 104 may be any form of computer-usable memory, including but not limited to random access memory (RAM), read-only memory (ROM), and non-volatile memory (e.g., flash memory, hard disk drives, solid state drives, compact discs (CDs), digital video discs (DVDs), and/or tape storage). Thus, memory 104 represents both main memory units, as well as long-term storage.

Memory 104 may store program instructions and/or data on which program instructions may operate. By way of example, memory 104 may store these program instructions on a non-transitory, computer-readable medium, such that the instructions are executable by processor 102 to carry out any of the methods, processes, or operations disclosed in this specification or the accompanying drawings.

As shown in FIG. 1, memory 104 may include firmware 104A, kernel 104B, and/or applications 104C. Firmware 104A may be program code used to boot or otherwise initiate some or all of computing device 100. Kernel 104B may be an operating system, including modules for memory management, scheduling and management of processes, input/output, and communication. Kernel 104B may also include device drivers that allow the operating system to communicate with the hardware modules (e.g., memory units, networking interfaces, ports, and busses), of computing device 100. Applications 104C may be one or more user-space software programs, such as web browsers or email clients, as well as any software libraries used by these programs. Memory 104 may also store data used by these and other programs and applications.

Network interface 106 may take the form of one or more wireline interfaces, such as Ethernet (e.g., Fast Ethernet, Gigabit Ethernet, and so on). Network interface 106 may also support communication over one or more non-Ethernet media, such as coaxial cables or power lines, or over wide-area media, such as Synchronous Optical Networking (SONET) or digital subscriber line (DSL) technologies. Network interface 106 may additionally take the form of one or more wireless interfaces, such as IEEE 802.11 (Wifi), BLUETOOTH®, global positioning system (GPS), or a wide-area wireless interface. However, other forms of physical layer interfaces and other types of standard or proprietary communication protocols may be used over network interface 106. Furthermore, network interface 106 may comprise multiple physical interfaces. For instance, some embodiments of computing device 100 may include Ethernet, BLUETOOTH®, and Wifi interfaces.

Input/output unit 108 may facilitate user and peripheral device interaction with example computing device 100. Input/output unit 108 may include one or more types of input devices, such as a keyboard, a mouse, a touch screen, and so on. Similarly, input/output unit 108 may include one or more types of output devices, such as a screen, monitor, printer, and/or one or more light emitting diodes (LEDs). Additionally or alternatively, computing device 100 may communicate with other devices using a universal serial bus (USB) or high-definition multimedia interface (HDMI) port interface, for example.

In some embodiments, one or more computing devices may be deployed in a networked architecture. The exact physical location, connectivity, and configuration of the computing devices may be unknown and/or unimportant to client devices. Accordingly, the computing devices may be referred to as "cloud-based" devices that may be housed at various remote locations.

Figure 2:
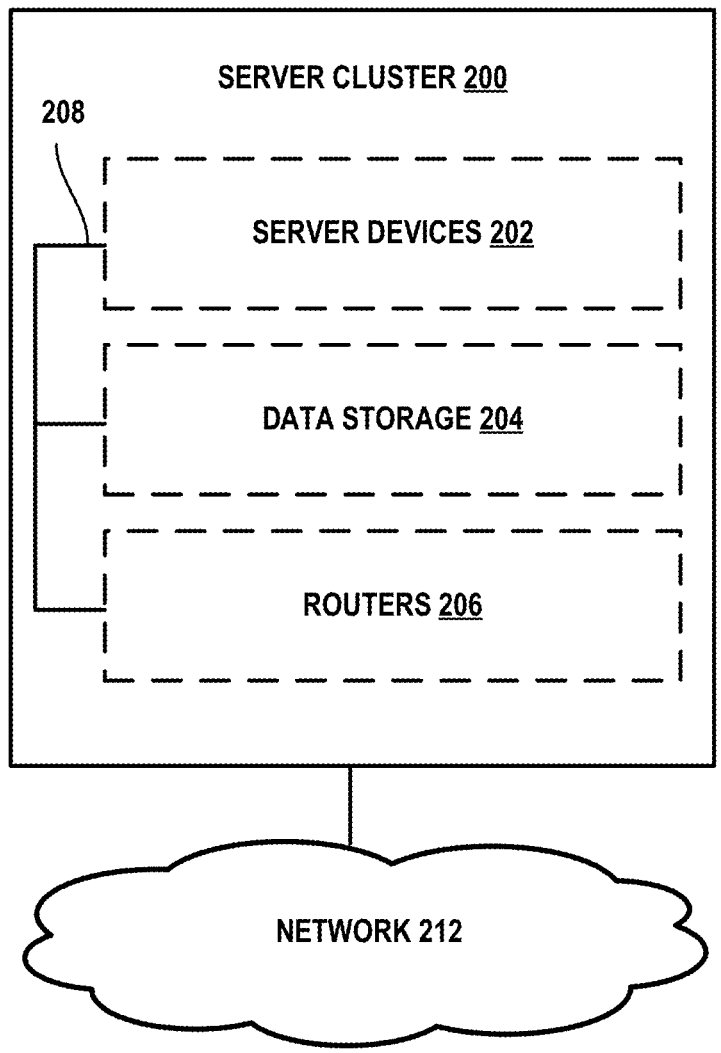
FIG. 2 illustrates a schematic drawing of a server device cluster, in accordance with example embodiments.

FIG. 2 depicts a cloud-based server cluster 200 in accordance with example embodiments. In FIG. 2, operations of a computing device (e.g., computing device 100) may be distributed between server devices 202, data storage 204, and routers 206, all of which may be connected by local cluster network 208. The number of server devices 202, data storages 204, and routers 206 in server cluster 200 may depend on the computing task(s) and/or applications assigned to server cluster 200.

For example, server devices 202 can be configured to perform various computing tasks of computing device 100. Thus, computing tasks can be distributed among one or more of server devices 202. To the extent that these computing tasks can be performed in parallel, such a distribution of tasks may reduce the total time to complete these tasks and return a result. For purpose of simplicity, both server cluster 200 and individual server devices 202 may be referred to as a "server device." This nomenclature should be understood to imply that one or more distinct server devices, data storage devices, and cluster routers may be involved in server device operations.

Data storage 204 may be data storage arrays that include drive array controllers configured to manage read and write access to groups of hard disk drives and/or solid state drives. The drive array controllers, alone or in conjunction with server devices 202, may also be configured to manage backup or redundant copies of the data stored in data storage 204 to protect against drive failures or other types of failures that prevent one or more of server devices 202 from accessing units of cluster data storage 204. Other types of memory aside from drives may be used.

Routers 206 may include networking equipment configured to provide internal and external communications for server cluster 200. For example, routers 206 may include one or more packet-switching and/or routing devices (including switches and/or gateways) configured to provide (i) network communications between server devices 202 and data storage 204 via cluster network 208, and/or (ii) network communications between the server cluster 200 and other devices via communication link 210 to network 212.

Additionally, the configuration of cluster routers 206 can be based at least in part on the data communication requirements of server devices 202 and data storage 204, the latency and throughput of the local cluster network 208, the latency, throughput, and cost of communication link 210, and/or other factors that may contribute to the cost, speed, fault-tolerance, resiliency, efficiency and/or other design goals of the system architecture.

As a possible example, data storage 204 may include any form of database, such as a structured query language (SQL) database. Various types of data structures may store the information in such a database, including but not limited to tables, arrays, lists, trees, and tuples. Furthermore, any databases in data storage 204 may be monolithic or distributed across multiple physical devices.

Server devices 202 may be configured to transmit data to and receive data from cluster data storage 204. This transmission and retrieval may take the form of SQL queries or other types of database queries, and the output of such queries, respectively. Additional text, images, video, and/or audio may be included as well. Furthermore, server devices 202 may organize the received data into web page representations. Such a representation may take the form of a markup language, such as the hypertext markup language (HTML), the extensible markup language (XML), or some other standardized or proprietary format. Moreover, server devices 202 may have the capability of executing various types of computerized scripting languages, such as but not limited to Perl, Python, PHP Hypertext Preprocessor (PHP), Active Server Pages (ASP), JavaScript, and so on. Computer program code written in these languages may facilitate the providing of web pages to client devices, as well as client device interaction with the web pages.

II. Example DNA Information System Architecture

Figure 3:
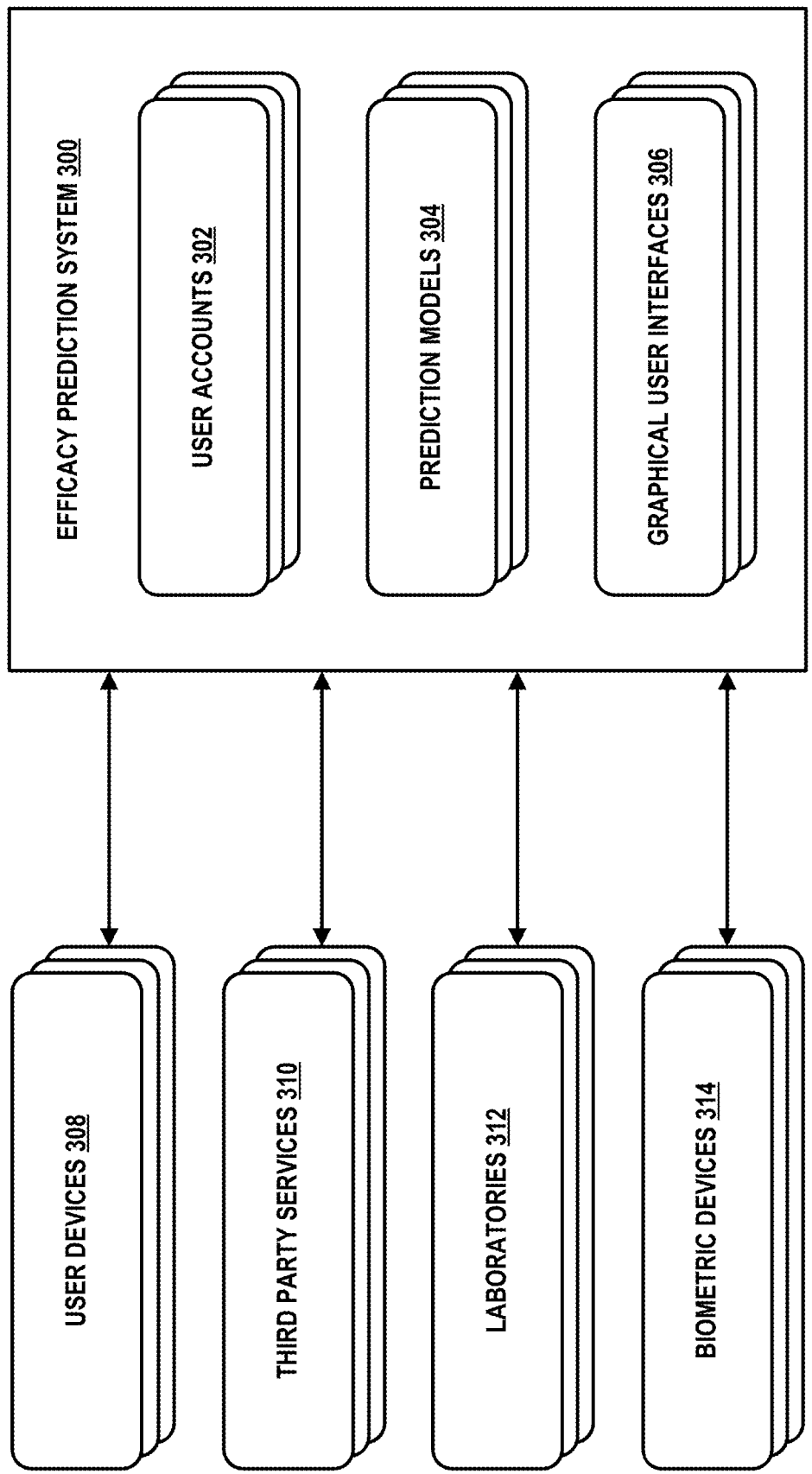
FIG. 3 depicts a DNA information system architecture, in accordance with example embodiments.

FIG. 3 depicts an efficacy prediction system architecture, in accordance with example embodiments. This architecture includes five main components, including efficacy prediction system 300, user devices 308, third-party services 310, laboratories 312, and biometric devices 314. These components may all be connected via one or more of point-to-point links, Personal Area Networks (PANs), Local-Area Networks (LANs), Wide-Area Networks (WANs) such as the Internet or cellular networks, cloud networks, and/or operational technology (OT) networks, among other possibilities.

Efficacy prediction system 300 may be, for example, a system that functions to predict the efficacy of compounds for health conditions of individuals. At a high level, efficacy prediction system 300 may function to receive respective information from numerous individuals in a group of individuals, each of whom has taken one or more compounds for the treatment of one or more health conditions. This group of individuals may provide their respective information voluntarily for a number of reasons, some of which may include enrolling in a study and opting into an information sharing program, among others.

Based on the information received from the group of individuals, the efficacy prediction system 300 may train prediction models, use the prediction models to make efficacy predictions for certain chemical compounds with respect to a given individual, and display those efficacy predictions to the given individual. Efficacy prediction system 300 may include various user accounts 302, prediction models 304, and a plurality of graphical user interfaces 306.

The information that efficacy prediction system 300 receives may take various forms. As one possibility, the information may take the form of genetic information for the individuals in the group. The genetic information itself may take various forms as well, examples of which include genotypes, haplotypes, genetic variants, copy number variations, phenotypes, polygenic risk scores, polygenic risk profiles, epigenetic data, genealogy information, and various genetic mutations such as insertions, deletions, missense, nonsense, and frameshift mutations, among others.

As another possibility, the information may take the form of biometric information for the individuals in the group. The biometric information may take various forms as well, examples of which include photoplethysmography data, oxygen saturation levels, arterial elasticity, peripheral elasticity, sleep information, glucose levels, blood pressure, accelerometry, actigraphy, ancestry data, population data, and medical history information, among others.

As yet another possibility, the information may take the form of feedback information for the individuals in the group. The feedback information may take various forms as well, examples of which include survey information (e.g., questionnaires with predefined questions and answers) and interviews conducted in a manner consistent with Real-World Evidence (RWE) accumulation. The feedback information may relate to individuals' responses to certain compounds when used recreationally or to treat certain health conditions, potential drug interactions, individuals' side effects, quality of life information, physical and/or emotional improvements, among other things.

As still yet another possibility, the information may take the form of efficacy information, which may take various forms as well, one example of which includes an indication of whether a given compound was effective for a given individual's health condition (e.g., whether and/or how well a particular cannabinoid achieved the individual's desired effect).

The information that efficacy prediction system 300 receives may take other forms as well.

Additionally, efficacy prediction system 300 may receive the information from various sources, depending on the type of information. As one example, efficacy prediction system 300 may receive genetic information from one or more providers, examples of which may be third-party services 310 and laboratories 312 which are described in further detail below. As another example, efficacy prediction system 300 may receive biometric information from one or more biometric devices, such as biometric devices 314 which are described in further detail below. As yet another example, efficacy prediction system 300 may receive feedback information and efficacy information from one or more user devices, such as user devices 308 which are described in further detail below. Efficacy prediction system 300 may receive the information from other sources as well. Further, it should be understood that efficacy prediction system 300 may receive any of the above information from any of the described sources.

User accounts 302 may take various forms, one example of which includes accounts that allow individuals to upload and/or send information to efficacy prediction system 300 via user devices 308. In this respect, efficacy prediction system 300 may provide an individual with the ability to create an account. Once the account is created, efficacy prediction system 300 may present the individual with one or more graphical user interfaces that are configured to allow the individual to upload and/or send information (e.g., any of the information described above) to efficacy prediction system 300. User accounts 302 may take other forms as well.

Prediction models 304 may take various forms. As one possibility, prediction models 304 may take the form of a model that is configured to group a plurality of individuals based on efficacy information and similarities in one or more of their respective genetic, biometric, and feedback information. In this respect, prediction model 304 may function to determine the relevant types of genetic, biometric, and/or feedback information that is predictive of the efficacy of a given compound for a given health condition. For example, prediction model 304 may receive efficacy information and one or more of genetic, biometric, and/or feedback information from a plurality of individuals and then use one or more machine learning techniques to group the individuals. In this way, the relevant information used to group the individuals may be some subset of the genetic, biometric, and/or feedback data. For instance, prediction model may determine that for a given compound, individuals with a particular genotype and a particular frameshift mutation experience similar efficacy. It should be understood that prediction model 304 may determine that any combination of genetic, biometric, and/or feedback information is predictive of efficacy for the given compound. Further, the one or more machine learning techniques may take various forms, examples of which may include K-Nearest Neighbors, K-means Clustering, Logistic Regression, Lasso Regression, Naive Bayes, Decision Tree, and Support Vector Machines, among others. Prediction model 304 may take other forms as well.

In some circumstances, the genetic, biometric, and/or feedback information that prediction model 304 receives may be vast. For instance, if an individual's genetic information includes the individual's entire genome, there may be billions of data points for each individual whose information is received. In these circumstances, prediction model 304 may undertake one or more pre-processing techniques to reduce the dimensionality of the information. Reducing the dimensionality of the information may take various forms, one example of which includes Principal Component Analysis (PCA). In this respect, prediction model 304 may use PCA to determine covariances in the information (i.e., determine the variables that are most relevant) and remove a subset of information related to less relevant variables. This may be advantageous in that prediction model 304 can apply the one or more machine learning techniques to a more focused set of information, which in turn may reduce network resources and the time at which an efficacy predication can be made. Reducing the dimensionality of the information may take other forms as well.

Graphical user interfaces 306 may take various forms, examples of which include one or more web-based and/or application-based graphical user interfaces configured to allow an individual to interact with efficacy prediction system 300 and perform functions such as (i) creating an account to upload and/or send information to efficacy prediction system 300 and (ii) viewing an efficacy prediction provided by efficacy prediction system 300, among others. Graphical user interfaces 306 may take other forms as well.

User devices 308 may take various forms, one example of which may include a plurality of computing devices 100, as described in FIG. 1. User devices 308 may be configured to carry out a plurality of actions, including but not limited to (i) setting up a user account 302 at efficacy prediction system 300, (ii) sending and/or uploading information to efficacy prediction system 300, (iii) viewing an efficacy prediction provided by efficacy prediction system 300 via graphical user interfaces 306. User devices 308 may take other forms as well.

Third-party services 310 may take various forms, examples of which may include various genetic information and/or biometric providers, such as 23ANDME® and ANCESTRY.COM®. Such third-party services 310 may offer a variety of services, including sending DNA test kits to users. These DNA test kits may include elements configured to receive DNA samples from individuals (e.g., test tubes for saliva deposits). Once an individual completes a DNA test kit and returns it to a third-party service 310, the third-party service 310 may send the DNA samples to laboratories 312. After the laboratories 312 process the DNA sample, they may send the raw DNA data back to third-party services 310, which in turn may provide the raw DNA data as genetic information to efficacy prediction system 300. Third-party services 310 may take other forms as well.

Laboratories 312 may take various forms, examples of which may include laboratories that receive DNA samples and analyze the samples to create raw DNA data. This raw DNA data may include some or all of a individual's genome in the form of a text file. Laboratories 312 may then provide this raw DNA data as genetic information to efficacy prediction system 300. Laboratories 312 may take other forms as well.

Biometric devices 314 may be configured to monitor one or more types of biometric information in a given individual and may take various forms, examples of which may include wearable devices (e.g., APPLE WATCH®, FITBIT®, GARMIN®, WHOOP®, etc.) and/or medical professional monitoring devices (e.g., glucose monitors, blood pressure monitors, etc.). Biometric devices 314 may take other forms as well.

As discussed above, it may be desirable for an individual to fully understand and comprehend the different mental and physical traits that could possibly be affected when using certain cannabinoid compounds. For instance, an individual's genetic information may indicate that a individual has a greater risk for anxiety in a stressful situation relative to other genotypes. This indication is determined by analyzing the individual's genotype at a particular polymorphism for a particular gene. For example, with respect to an individual's propensity for anxiety, one could analyze the individual's genotype at (i) the polymorphism rs1049353 for the CNR1 gene, (ii) the polymorphism rs324420 at the FAAH gene, and (iii) the 5-HTTLPR polymorphism for the SLC6A4 gene.

Along with anxiety, there are a number of traits that may be affected by cannabinoid usage. Each of these traits has an associated polymorphism for different genes. For purposes of this disclosure, the terms "SNP" and "polymorphism" may be used interchangeably.

A. Anxiety

Anxiety is a common disorder experienced by many individuals. While the study behind the causes and effects of anxiety are ever changing, there have been several SNPs discovered that relate to the interaction of anxiety and cannabinoids. For example, the SNP rs1049353 for the CNR1 gene is associated with activation of specific brain areas (the insula and amygdala). The effect of this related to how one gauges visual, emotional, and social cues. Examples include facial expressions that change from anger to sadness or fear; happiness to sadness or fear; and neutral. Another example is the SNP rs324420 for the FAAH gene, which is associated with how an individual's endocannabinoid system (ECS) is related to specific neural mechanisms which may impact complex behavioral processes related to risk for addiction, dependence, and obesity. Yet another example is the SNP 5-HTTLPR for the SLC6A4 gene, which is associated with the development of anxiety for youth users of cannabis. By analyzing these SNPs, DNA information system 300 may be able to effectively recommend certain cannabinoid compounds and/or formulations tailored to a user's DNA.

B. Bipolar Disorder

Bipolar disorder, or manic depression, is a serious brain illness that causes unusual shifts in mood, energy, activity, and the ability to carry out daily activities. Individuals suffering from bipolar disorder experience periods of intense emotion, changes in sleep, and unusual behavior, known as episodes. Episodes can be categorized as either manic (more energetic and "up" than normal) or depressive (more low energy and "down" than normal). While research surrounding bipolar disorder is ever changing, researchers have identified a SNP associated with the risk for developing bipolar disorder. For example, the SNP rs41311993 for the CNR2 gene is associated with the risk for developing bipolar disorder. Using this association, DNA information system 300 can recommend a cannabinoid formulation that will react positively with a user that has a lower/higher risk of developing bipolar disorder.

C. Cognitive Function

Cognitive function may, for example, relate to a user's ability of their brain to process information and knowledge. While this is a general trait, researchers have identified SNPs that indicate how cannabis may affect a user's cognitive function. In one example, the SNP rs1049353 for the CNR1 gene is associated with lower performance of executive function and sustained attention. Thus, depending on their endocannabinoid genotype, some users may experience an elevated risk of not being able to sustain attention when using cannabis. In another example, the SNP rs4680 for the COMT gene is associated with risk of structural brain changes following cannabis use. Users that have an at-risk genotype for this SNP (e.g., homozygous alleles, such as (A/A)), may want to consult with a specialist in cognitive function before using cannabis. In yet another example, the SNP rs12199654 for the MAPK14 gene is associated with a risk of decreased white matter brain volume from cannabis use, which may result in impairing a user's cognitive function. In another example, the SNP rs7834206 for the NRG1 gene is associated with auditory reception when using cannabis. Users with heterozygous alleles (C/A) may be more likely to have auditory discrepancies after using cannabis when compared to users with other genotypes. In yet another example, the SNP 5-HTTLPR for the SLC6A4 gene is associated with a user's focus, visual interpretation of their environment, and decision making. Users with homozygous alleles (L'/L') might not experience a decrease in brain performance when using cannabis.

D. Depression

Depression may, for example, relate to how a user feels, thinks, and acts. Specifically, depression is a long-term mental degradation that can affect the way a user functions in daily life. Depression can further be characterized by feeling tearful, irritable, and having diminished interest or pleasure in activities every day; significant weight loss/decrease or increase in appetite; inability to get to sleep or difficulty staying asleep or sleeping too much; problems with sitting or a slowing of one's movements; talking very quietly with slowed speech; fatigue; tiredness; feelings of worthlessness; diminished ability to think or concentrate; recurrent thoughts of death (not just fear of dying); recurrent suicidal ideas without a specific plan; or a suicide attempt or creating a specific plan for committing suicide. Due to the severity of depression symptoms, it is beneficial to have an understanding of how cannabis may affect users that have a particular genotype. For example, the SNP rs1049353 for the CNR1 gene is associated with depression—specifically, how a user reacts to certain antidepressants such as citalopram. Users that have heterozygous alleles (C/T) may have a decrease likelihood of responding to antidepressants. In another example, the SNP rs2023239 for the CNR1 gene is associated with depression generally. Users that have homozygous alleles (T/T) may experience a higher likelihood of exacerbating pre-existing symptoms of depression when using cannabis. In yet another example, the SNP rs806377 for the CNR1 gene is associated with how a user responds to positive emotional stimuli. Users with homozygous alleles (T/T) may experience a higher amount of positive emotions after a positive event than people with heterozygous alleles. In yet another example, the SNP rs324420 for the FAAH gene is associated with white matter integrity in the brain and increased reports of depression and apathy in cannabis users. Users with homozygous alleles (CC) may experience decreased white matter in the brain and weakened brain structure when cannabis is used at a young age. This information may be particularly useful when determining which cannabinoid formulation to recommend to a user.

E. Impulsive Behavior

Impulsive behavior may, for example, relate to making decisions without thinking of the results and/or consequences beforehand. Impulsive behavior has many causes, which can include mental disorders such as hyperactivity disorder or personality disorders, such as borderline personality disorder. Cannabis usage may also cause impulsivity for certain users. For example, the SNP rs1049353 for the CNR1 gene is associated with adolescent psychosocial adversity, which is how one responds and/or adapts to family or relationship problems, health problems, school and other structural worries, and how they relate to impulsive behavior. Users with a genotype containing heterozygous alleles (C/T) may have an elevated risk of impulsive behavior when using cannabis. In another example, the SNP rs806379 for the CNR1 gene is also associated with adolescent psychosocial adversity. Users with homozygous alleles (A/A) that experienced early psychosocial adversity may have a higher risk of impulsive behavior. In yet another example, the SNP rs1611115 for the DBH gene is associated with impulsivity after cannabis consumption. Users with homozygous alleles (C/C) might not have increased impulsivity after cannabis use, while users with heterozygous alleles may have increased impulsivity after cannabis use. In yet another example, the SNP rs221533 for the NRG1 gene is associated with lower inhibition and significantly riskier decision making. Users with heterozygous alleles (T/C) may have a lower risk of having behaviors associated with risky decision making when using cannabis. In yet another example, the SNP rs28363170 for the SLC6A3 gene is also associated with impulsivity when using cannabis. Users with homozygous alleles (10R/10R) may have a lower risk of impulsivity after consuming cannabis compared to users with heterozygous alleles.

F. Memory Impairment

Memory impairment may, for example, relate to a person's ability to store information in their brain. For example, the SNP rs1049353 for the CNR1 gene is associated with varying brain awareness states, which is related to working memory ability and other cognitive functions. Users with heterozygous alleles (C/T) may have a normal state of awareness when compared to users with a different genotype. In another example, the SNP rs1406977 for the CNR1 gene is associated with performance on working memory tasks when using cannabis. Users with homozygous alleles (T/T) may be less likely to experience working memory impairments after use of THC.

G. Metabolic Function

Metabolic function may, for example, relate to how a user's cells breaks down materials from food to energy. Metabolic function may vary in users that are consuming cannabis. For example, the SNP rs1045642 for the ABCB1 gene is associated with THC levels and THC metabolites in cannabis users. Users with homozygous alleles (T/T) may have two-fold lower blood THC levels after consuming THC relative to people with a different genotype. In another example, the SNP rs1057910 for the CYP2C9 gene is associated with how oral THC is processed or metabolized in the body. Users with homozygous alleles (A/A) are typically no more sensitive to oral THC.

H. Migraines

Migraines may, for example, relate to severe headaches that occur on one side of the head. Migraines can cause extreme discomfort and symptoms such as nausea and oversensitivity to lights and sounds. Research indicates that cannabis usage may have an effect on migraines in certain individuals. For example, the SNP rs806366 for the CNR1 gene is associated with a user's susceptibility to migraines. Users with homozygous alleles (T/T) may be more likely to develop migraines after stressful events. This is beneficial information because a medical provider can prescribe an appropriate dose if the provider is aware that the user is more likely to develop migraines.

I. Motor Control

Motor control may, for example, relate to the process of creating and sending purposeful, voluntary movements throughout the body. Research indicates that the consumption of cannabis may have profound effects on a user's motor control. For example, the SNP rs1130233 for the AKT1 gene is associated with the degree of impairment in a user's psychomotor control and/or motor coordination after consumption of THC. Users with heterozygous alleles (C/T) may develop impaired motor coordination and slowed down thinking after consuming THC.

J. Opioid Effects

Opioids are, for example, a class of drugs created from the opium poppy plant. The plants are harvested and used in various types of medications because they contain a chemical that relaxes the body, and helps to relieve pain. Examples of opioids include Hydrocodone, Oxycodone, Oxymorphone, Morphine, Fentanyl, and Codeine. Research indicates that particular genetic markers may affect how a user reacts to opioids. For example, the SNP rs324420 for the FAAH gene is associated with having adverse opioid effects when combined with how a user's endocannabinoid system modulates, by way of such cannabinoids such as anandamide. Users with homozygous alleles (C/C) may have a lower risk of experienced side effects from opioids relative to people with a different genotype.

K. Pain

Pain may, for example, relate to the unpleasant and corresponding emotional reaction in response to injury or tissue damage. Pain is a signal sent through the spinal cord, to a user's brain, alerting her that something is wrong in her body. Pain can be difficult to diagnose as it can manifest itself in different ways for different people. For example, the SNP rs324420 for the FAAH gene is associated with pain sensitivity and use of postoperative analgesia. Users with homozygous alleles (C/C) may have higher pain sensitivity to cold temperatures and more need for analgesia during periods of acute pain, such as after an operation. This information is beneficial when a provider is prescribing cannabis after an operation.

L. Psychosis

Psychosis may, for example, relate to a user's propensity for becoming disconnected from reality. Psychosis from cannabis can cause delusions, which are strong beliefs that don't make sense and/or are not consistent with the user's actual beliefs. Research indicates that cannabis may have a more profound effect on users with particular genetic markers. For example, the SNP rs1130233 for the AKT1 gene is associated with the risk of psychosis-like effects (e.g., include delusion, delirium and confusion) after consuming THC. Users with heterozygous alleles (C/T) may have an increased risk of experience acute psychosis-like effects after consuming THC. In another example, the SNP rs2494732 for the AKT1 gene is associated with the risk of psychotic episode in users that consume cannabis. Users with homozygous alleles (T/T) may have a lower risk of experiencing psychotic disorder effects after consuming THC. In yet another example, the SNP rs6265 for the BDNF gene is associated with the onset of a psychotic disorder at a young age. Users with homozygous alleles (G/G) may not be at risk for onset psychosis if the user is already predisposed to developing psychosis.

In yet another example, the SNP rs4680 for the COMT gene is also associated with psychosis-like effects (e.g., delusion, delirium, and confusion) after consuming THC. Users with homozygous alleles (A/A) may be less likely to experience psychosis-like effects after consuming THC relative to people with different genotypes. In another example, the SNP rs1076560 for the DRD2 gene is associated with a greater risk of developing psychosis (e.g., having regular hallucinations and delusions) in cannabis users. In yet another example, the SNP rs2494732 for the AKT1 gene is associated with a risk of a psychotic disorder and cognitive disabilities, including verbal memory and sustained attention impairments. Users with homozygous alleles (T/T) may have a lower risk of psychotic disorder and a lower risk of memory and attention impairments after consuming THC than users with a different genotype. This information may be particularly beneficial as it may prevent a user that is predisposed to psychosis from overdosing on THC.

M. Psychotic Like Effects

Psychotic like effects may, for example, include delusions and delirium caused by cannabis usage. Research indicates that cannabis use can cause schizophrenia, an illness that can cause a person to feel as if they have lost touch with reality. Research also indicates that certain genetic markers can indicate whether an individual is more likely to experience psychotic like effects when consuming cannabis. For example, the SNP 5-HTTLPR for the gene SLC6A4 is associated with psychotic like effects in user with bipolar disorder when that user consumes cannabis.

N. Sleep Quality

Sleep quality may, for example, relate to the amount of time a user sleeps, the amount of times a user wakes up during the night, and the amount of time it takes a user to fall asleep. Research indicates certain genetic markers are related to sleep quality. For example, the SNP rs324420 for the FAAH gene is associated with poorer sleep quality among young cannabis users who exhibit depression symptoms. Users with homozygous alleles (C/C) may have an increased risk of poor sleep quality while using certain cannabinoid formulations.

However, as indicated above, the efficacy of a given compound to treat a given health condition, is likely based on other factors beyond the presence and/or absence of certain SNPs in an individual's genetic information. Accordingly, there is a need to analyze and model additional information related to a plurality of individuals' genetic, biometric, and/or feedback data in order to provide improved predictions regarding the efficacy of a given compound for a given individual.

III. Example Operations

As discussed above, the human genome is complex and contains 6.4 billion base pairs. However, only a small fraction of these base pairs impacts how a given individual will react to certain chemical compounds when being treated for a given health condition. Accordingly, it may be advantageous to use efficacy prediction modeling in order to provide individuals with an indication of the likelihood that a given chemical compound will be effective in treating a given health condition.

Figure 4:
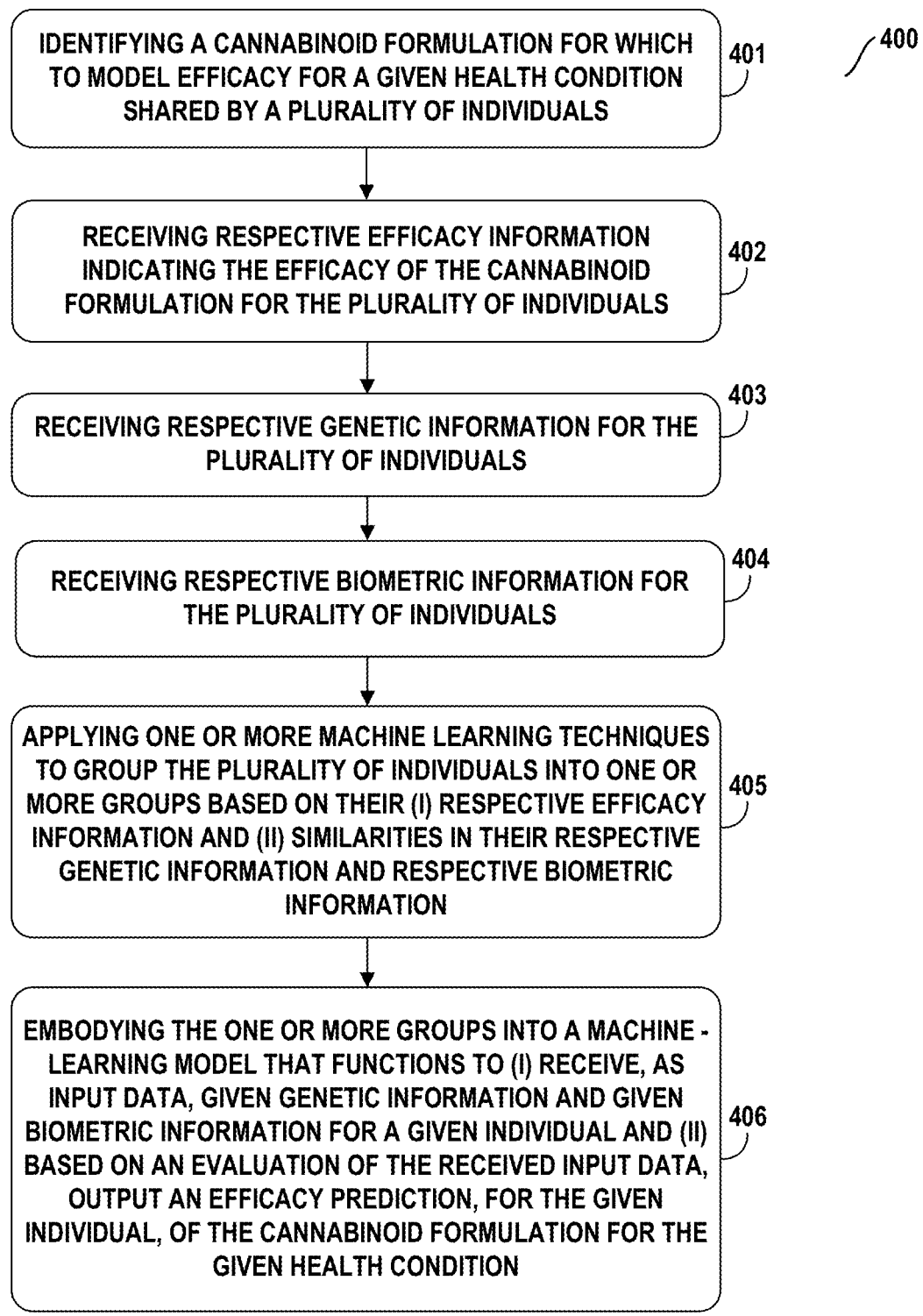
FIG. 4 depicts a flow chart, in accordance with example embodiments.

FIG. 4 is a flow chart illustrating an example method 400. The process illustrated by FIG. 4 may be carried out by an efficacy prediction system, such as efficacy prediction system 300 described above with respect to FIG. 3. However, the process can be carried out by other types of systems, devices, or device subsystems. For example, the process could be carried out by a portable computer, such as a laptop or a tablet device.

The embodiments of FIG. 4 may be simplified by the removal of any one or more of the features shown therein. Further, these embodiments may be combined with features, aspects, and/or implementations of any of the previous figures or otherwise described herein.

Block 401 may involve identifying a cannabinoid formulation for which to model efficacy for a given health condition shared by a plurality of individuals. The cannabinoid formulation for which to model efficacy for a given health condition may be identified in various ways, one example of which may first include identifying a given health condition that is shared by a plurality of individuals and then identifying a cannabinoid formulation that has been shown to fully and/or partially remedy the given health condition. For example, if the plurality of individuals is suffering from sleep apnea, a cannabinoid formulation may be identified that is likely to remedy the symptoms of sleep apnea. The cannabinoid formulation for which to model efficacy for a given health condition may be identified in other ways as well.

Block 402 may involve receiving respective efficacy information indicating the efficacy of the cannabinoid formulation for the plurality of individuals. The function of receiving respective efficacy information indicating the efficacy of the cannabinoid formulation for the plurality of individuals may take various forms. As one possibility, receiving respective efficacy information may involve collecting efficacy information from each individual in the plurality of individuals as each individual uses the identified cannabinoid formulation to treat the given health condition. In this way, each individual in the plurality of individuals may, after using the cannabinoid formulation, provide an indication that the cannabinoid formulation was effective or ineffective at treating the given health condition. The function of receiving respective efficacy information indicating the efficacy of the cannabinoid formulation for a plurality of individuals may take other forms as well.

Further, the efficacy information may take various forms. As one example, the efficacy information may take the form of a binary indication of whether the given cannabinoid formulation was effective or ineffective to treat the given health condition. As another example, the efficacy information may take the form of a numerical indication for how effective the cannabinoid formulation was at treating the given health condition. For instance, one of the plurality of individuals may provide efficacy information that indicates the cannabinoid formulation was a 4 out of 5 in terms of effectiveness. Other examples exist. The efficacy information may take other forms as well.

Block 403 may involve receiving respective genetic information for the plurality of individuals. The function of receiving respect genetic information for the plurality of individuals may take various forms. As one possibility, receiving respective genetic information for the plurality of individuals may involve receiving respective genetic information directly from each of the individuals in the plurality of individuals. In this way, each individual in the plurality of individuals may provide his or her respective genetic information (e.g., via one or more user devices, such as user devices 308 as described above with respect to FIG. 3). As another possibility, receiving respective genetic information for the plurality of individuals may involve receiving respective genetic information from one or more third-party services, such as third-party services 310 described above with respect to FIG. 3. As yet another possibility, receiving respective genetic information for the plurality of individuals may involve receiving respective genetic information from one or more laboratories, such as laboratories 312 as described above with respect to FIG. 3. The function of receiving respective genetic information for the plurality of individuals may take other forms as well.

Block 404 may involve receiving respective biometric information for the plurality of individuals. The function of receiving respective biometric information for the plurality of individuals may take various forms. As one possibility, receiving respective biometric information for the plurality of individuals may involve receiving respective biometric information directly from each of the individuals in the plurality of individuals. In this way, each individual in the plurality of individuals may provide his or her respective biometric information (e.g., via one or more user devices, such as user devices 308 as described above with respect to FIG. 3). As another possibility, receiving respective biometric information for the plurality of individuals may involve receiving respective biometric information from one or more biometric devices, such as biometric devices 314 as described above with respect to FIG. 3. The function of receiving respective biometric information for the plurality of individuals may take other forms as well.

Although not shown, in some example embodiments, the method may additionally involve receiving respective feedback information for the plurality of individuals. The function of receiving respective feedback information for the plurality of individuals may take various forms. As one possibility, receiving respective feedback information for the plurality of individuals may involve receiving respective feedback information directly from each of the individuals in the plurality of individuals. In this way, each individual in the plurality of individuals may provide his or her respective feedback information (e.g., via one or more user devices, such as user devices 308 as described above with respect to FIG. 3). The function of receiving respective feedback information for the plurality of individuals may take other forms as well.

As discussed above, in some circumstances, the received information of the plurality of individuals (e.g., genetic, biometric, and/or feedback) may be so vast or multidimensional that the information is unfit as an input to the one or more machine learning techniques. In these circumstances, the method may optionally involve reducing the dimensionality of the information prior to applying the or more machine learning techniques. The function of reducing the dimensionality of the information may take various forms, one example of which includes Principal Component Analysis (PCA). In this respect, the efficacy prediction system may use PCA to determine covariances in the information (i.e., determine the variables that are most relevant) and remove a subset of information related to less relevant variables. The function of reducing the dimensionality of the information may take other forms as well.

Further, the efficacy prediction system may reduce the dimensionality of all or a subset of the various types of received information. As one example, if the received genetic information contains over a million data points and the received biometric information only contains a few dozen data points, the efficacy prediction system may only reduce the dimensionality of the genetic information. As another example, if the received genetic information and the received biometric information both contain a large number of data points, the efficacy prediction system may reduce the dimensionality of both the genetic information and the biometric information.

Additionally, the efficacy prediction system may reduce the dimensionality of the received information together or separately. As one example, the efficacy prediction system may first combine the received genetic information and the received biometric information into a single dataset and then reduce the dimensionality of the combined dataset. As another example, the efficacy prediction system may reduce the dimensionality of each type of information separately and then afterwards combine the reduced datasets into one combined dataset.

In example embodiments where the efficacy prediction system also receives respective feedback information from the plurality of individuals, the efficacy prediction system may also reduce the dimensionality of the feedback information in a similar manner as described above with respect to the received genetic and biometric information.

Block 405 may involve applying one or more machine learning techniques to group the plurality of individuals into one or more groups based on their (i) respective efficacy information and (ii) similarities in their respective genetic information, respective biometric information, and/or respective feedback information. For example, the efficacy prediction system may apply a clustering technique (sometimes referred to as a cluster analysis) that group the plurality of individuals into one or more groups based on one or more features included in their respective genetic, biometric, and/or feedback information, such that the individuals in each respective group have similar features to one another.

The one or more machine learning techniques may take various forms. As one example, the one or more machine learning techniques include a clustering technique such as K-Nearest Neighbor (KNN) or k-means clustering technique. The machine learning technique may take other forms as well, examples of which include Logistic Regression, Lasso Regression, Naive Bayes, Decision Tree, and Support Vector Machines, among others.

Regardless of the machine learning technique(s) utilized, the one or more machine learning techniques may function to group the plurality of individuals into one or more groups based on their respective efficacy information and similarities in their respective genetic information, respective biometric information, and/or respective feedback information.

As just one example, the one or more machine learning techniques may first group the plurality of individuals into one or more groups based on their respective efficacy information. In this respect, each of the individuals may have respective efficacy information that indicates whether the given cannabinoid formulation was effective (or an extent to which it was effective) or ineffective. In turn, the one or more machine learning techniques may group the individuals that have efficacy information that indicates the given cannabinoid formulation was effective and group the individuals that have efficacy information that indicates the given cannabinoid formulation was ineffective.

Next, the one or more machine learning techniques may create subgroups of individuals with each of the created groups that share similarities in their respective genetic information and respective biometric information. For instance, the one or more machine learning techniques may create a group where each of the individuals in the group have genetic information that includes SNP that indicates a likelihood that the individual will experience anxiety when using cannabis and biometric information that includes blood pressure levels that indicate increased blood pressure when using cannabis. The one or more machine learning techniques may create many such groups where each of the individuals in the groups share genetic information and/or biometric information.

In example embodiments where the efficacy prediction system also receives respective feedback information from the plurality of individuals, the one or more machine learning techniques may function to group the plurality of individuals into one or more groups based on their respective efficacy information and similarities in their respective genetic information, respective biometric information, and/or respective feedback information. The one or more machine learning techniques may accomplish this in a similar manner as above (e.g., grouping individuals based on similarities in their respective feedback information). For example, some individuals with positive efficacy information may be grouped together in a group based at least in part on their respective genetic information that indicates a similar gene (or combination of genes) in combination with similar feedback information (e.g., an indication of a particular symptom of poor sleep, etc.). The plurality of individuals may be clustered together based on combinations of these and other similar features as well.

Block 406 may involve embodying the one or more groups into a machine learning model that functions to (i) receive, as input data, given genetic information and given biometric information for a given individual and (ii) based on an evaluation of the received input data, output an efficacy prediction, for the given individual, of the cannabinoid formulation for the given health condition. In this respect, the one or more groups may be used as the training data for a machine learning model. Accordingly, once the machine learning model is trained, it can be used to provide an efficacy prediction to a given individual experiencing a given health condition. To accomplish this, the efficacy prediction system may perform functions involving (i) receiving a request to provide an efficacy prediction for a cannabinoid formulation for a given health condition experienced by a given individual, (ii) receiving, as input data, given genetic information for the given individual, (iii) receiving, as input data, given biometric information for the given individual, (iv) using the machine learning model, and (v) providing the efficacy prediction to the given individual. The process of providing an efficacy prediction to a given individual is described in further detail below with respect to FIG. 5.

Figure 5:
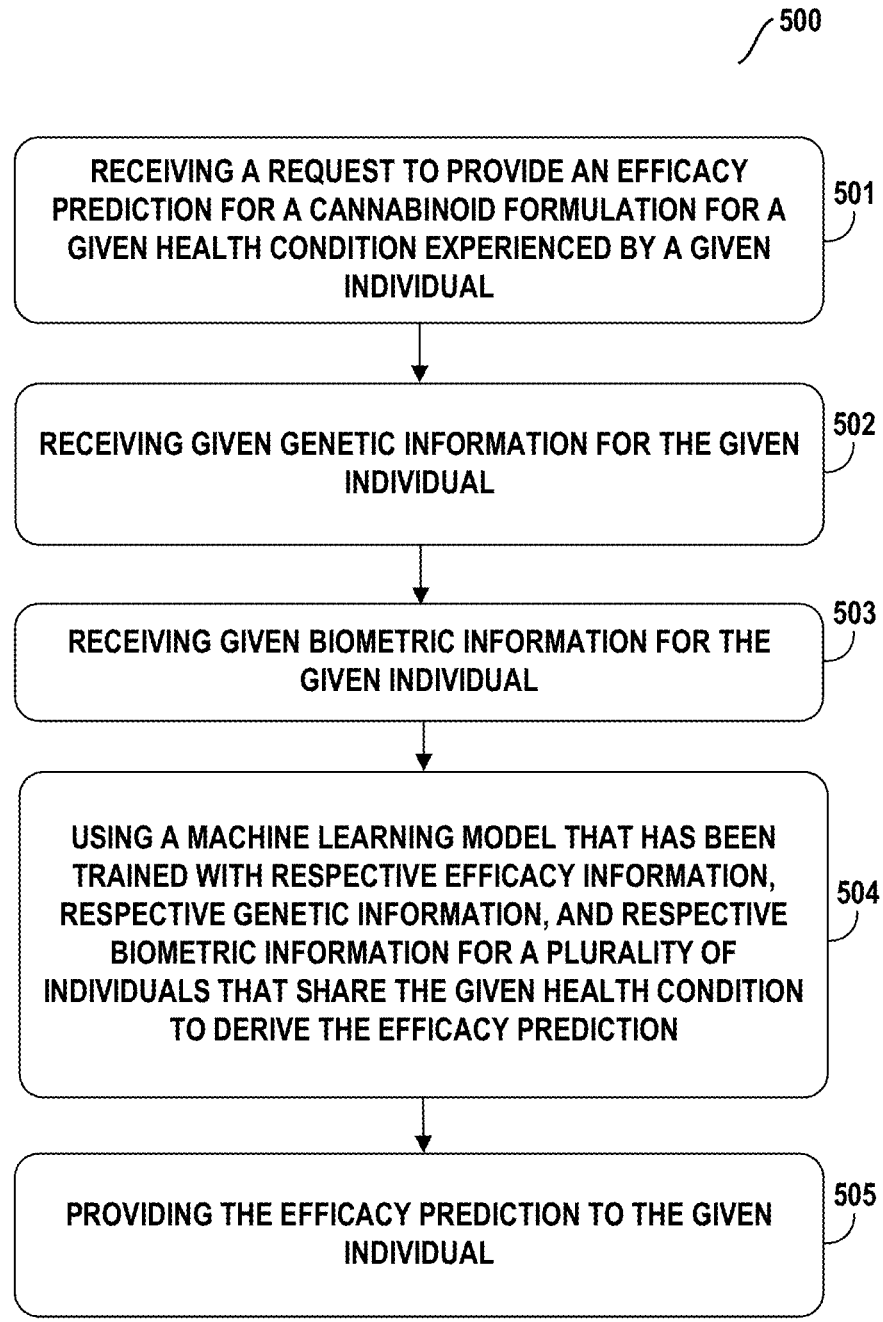
FIG. 5 depicts a flow chart, in accordance with example embodiments.

FIG. 5 is a flow chart illustrating an example method 500. The process illustrated by FIG. 5 may be carried out by an efficacy prediction system, such as efficacy prediction system 300 described above with respect to FIG. 3. However, the process can be carried out by other types of systems, devices, or device subsystems. For example, the process could be carried out by a portable computer, such as a laptop or a tablet device.

The embodiments of FIG. 5 may be simplified by the removal of any one or more of the features shown therein. Further, these embodiments may be combined with features, aspects, and/or implementations of any of the previous figures or otherwise described herein.

Block 501 may involve receiving a request to provide an efficacy prediction for a cannabinoid formulation for a given health condition experienced by a given individual. The function of receiving a request to provide an efficacy prediction for a cannabinoid formulation for a given health condition experienced by a given individual may take various forms, one example of which may include receiving the request to provide an efficacy prediction from a user device (e.g., one of user devices 308) associated with the given individual. For example, as described above, the given individual may have created an account with the efficacy prediction system that allows the given individual to submit the request for an efficacy prediction. In this respect, the given individual may access one or more graphical user interfaces (e.g., graphical user interfaces 306) and browse a plurality of potential cannabinoid formulations. Once the given individual has identified a cannabinoid formulation for which a request is desired, the given individual may submit a request for an efficacy prediction. The function of receiving a request to provide an efficacy prediction for a cannabinoid formulation for a given health condition experienced by a given individual may take other forms as well.

Block 502 may involve receiving given genetic information from the given individual. The function of receiving given genetic information for the given individual may take various forms. As one possibility, the given genetic information may be received from a user device (e.g., computer or smart phone) of the given individual. In this respect, the given individual may have access to his or her own genetic information and send the genetic information to the efficacy prediction system over a communication path such as the Internet. As another possibility, the given genetic information may be received from a third-party service (e.g., one of third-party services 310). In this respect, the given individual may request that the third-party service send the given individual's genetic information to the efficacy prediction system. This request may take various forms, one example of which may include linking the given individual's account with the third-party service with the given individual's account with the efficacy prediction system, which in effect authorizes the third-party service to send the given individual's genetic information to the efficacy prediction system. As yet another possibility, the given genetic information may be received from a laboratory (e.g., one of laboratories 312). In this respect, the given individual may provide a genetic sample to the laboratory and request that any genetic information derived from the sample be sent to the efficacy prediction system. The function of receiving given genetic information for the given individual may take other forms as well.

Block 503 may involve receiving given biometric information for the given individual. The function of receiving given biometric information for the given individual may take various forms. As one possibility, the given biometric information may be received from a biometric device configured to monitor biomarkers of the given individual. As one example, the given individual may have an APPLE WATCH® that is configured to monitor the given individual's heart rate and oxygen saturation levels. In this respect, the given individual may configure the APPLE WATCH® to share such biometric information with the efficacy prediction system either directly or indirectly via one or more user devices of the given individual. As another example, the given individual may have an embedded glucose monitor that is configured to monitor the given individual's glucose levels. In this respect, the given individual may configure the glucose monitor to share his or her glucose levels with the efficacy prediction system. Many other examples exist. The function of receiving given biometric information for the given individual may take other forms as well.

In some example embodiments, method 500 may additionally involve receiving given feedback information for the given individual. The function of receiving given feedback information for the given individual may take various forms. As one possibility, the given feedback information may be received from a user device of the given individual. In this respect, the given individual may provide a written description of certain symptoms or information related to the given health condition experienced by the given individual. The given individual may provide the written description in various ways, one example of which may include entering the written description on a user device of the given individual and sending the written description to the efficacy prediction system. The function of receiving given feedback information for the given individual may take other forms as well.

Block 504 may involve using a machine learning model that has been trained with respective efficacy information, respective genetic information, and respective biometric information for a plurality of individuals that share the given health condition to derive the efficacy prediction. The machine learning model used may take various forms, one example of which may include the prediction model trained by the efficacy prediction system described above with respect to FIGS. 3 and 4. The machine learning model may take other forms as well.

The function of using a machine learning model that has been trained with respective efficacy information, respective genetic information, and respective biometric information for a plurality of individuals that share the given health condition to derive the efficacy prediction may take various forms. As one possibility, where the machine learning model is the prediction model described above, using the machine learning model may involve determining (e.g., via a clustering analysis as discussed above) the group or groups of individuals that the given individual is most similar to based on the received genetic information and received biometric information. For instance, if the given individual has similar genetic information and biometric information as group of individuals that indicated the given cannabinoid formulation was effective for the given health condition, the machine learning model may derive an efficacy prediction that indicates the given cannabinoid formulation will likely be effective based on the given individual's similarity to the group of individuals for whom the formulation was effective. The function of using a machine learning model that has been trained with respective efficacy information, respective genetic information, and respective biometric information for a plurality of individuals that share the given health condition to derive the efficacy prediction may take other forms as well.

The efficacy prediction may also take various forms. As one example, the efficacy prediction may take the form of a binary indication of efficacy (e.g., an indication that the given cannabinoid formulation will likely be effective or ineffective for the given individual). As another example, the efficacy prediction may take the form of an efficacy indication that takes into account the degree of similarity in DNA markers between the given individual and the other individuals with similar genetic information and biometric information. In this respect, the efficacy prediction may include, in addition to an indication of whether the given cannabinoid formulation will likely be effective, an indication of how similar DNA markers of the given individual are to the other individuals with similar genetic information and biometric information (e.g., an indication that the given individual has a 93% DNA match with the other individuals for whom the formulation was effective). The efficacy prediction may take other forms as well.

Block 505 may involve providing the efficacy prediction to the given individual. The function of providing the efficacy prediction to the given individual may take various forms. As one possibility, providing the efficacy prediction to the given individual may involve providing the efficacy prediction and associated information via a graphical user interface on one of the given individual's user devices.

Figure 6:
FIG. 6 depicts a graphical user interface showing efficacy information for a given cannabinoid formulation, in accordance with example embodiments.

As one illustrative example, FIG. 6 depicts an example graphical user interface 600 that may be presented to the user. As shown, the example graphical user interface 600 includes an indication of a cannabinoid formulation 602, a cannabinoid profile pane 604, a DNA alignment pane 606, a metabolism DNA pane 608, a prescription drug interactions pane 610, a supplement interactions pane 612, and a reviews pane 614.

The indication of the cannabinoid formulation 602 may show the cannabinoid formulation for which the given individual has requested an efficacy prediction. As shown, cannabinoid formulation 602 shows the name of the cannabinoid formulation (e.g., the manufacturer's name), the delivery form of the cannabinoid formulation (e.g., tincture), and the amount of the cannabinoid formulation (e.g., 1500 mg).

Cannabinoid profile pane 604 may shows suggested attributes of a cannabinoid formulation to treat the given health condition based on the given individual's genetic information. For example, as shown, the given individual's genetic information suggests that the given individual should be seeking a cannabinoid formulation that has a CBD/THC ratio between 20:1 and 4:1, consist of less than 0.03% CBD, linalool as the primary terpene, and beta-caryophyllene as the secondary terpene.

DNA alignment pane 606 may show the percentage of match of the cannabinoid formulation to the given individual's cannabinoid profile. For example, as shown, the cannabinoid formulation is an 82% match to the given individual's cannabinoid profile.

Metabolism DNA pane 608 may show information related to the given individual's metabolism and an associated dosing recommendation. For example, as shown, the given individual's genetic information indicates that the given individual's metabolism is slower than average and thus a lower dosage should be considered for the cannabinoid formulation.

Prescription drug interactions pane 610 may show potential interactions between the cannabinoid formulation and any other medications the given individual is currently prescribed. As shown, there are no known interactions between the cannabinoid formulation shown in FIG. 6 and any medications the given individual is currently prescribed (to the extent they exist).

Supplement interactions pane 612 may show potential interactions between the cannabinoid formulation and any other supplements the given individual is currently taking.

Reviews pane 614 may show reviews of other individuals that have used the cannabinoid formulation and have similar genetic information as the given individual. In this respect, the information shown in reviews pane 614 may be derived from the efficacy prediction. For example, as shown, reviews pane 614 shows an overall review of 4.0 out of 5 based on 365 rating for the cannabinoid formulation. In addition, reviews pane 614 shows a breakdown of the DNA similarity between the given individual and the other individuals that provided reviews of the cannabinoid formulation. As shown, the given individual shares 93% of the same DNA with the individuals that provided reviews of the cannabinoid formulation. Reviews pane 614 provides a further breakdown, indicating that the given individual shares 94% of the same DNA with individuals that provided five star reviews, 95% of the same DNA with individuals that provided four star reviews, 95% of the same DNA with individuals that provided three star reviews, 91% of the same DNA individuals that provided two star reviews, and 89% of the same DNA with individuals that provided one star reviews. These percentages are derived based on efficacy prediction(s) determined by the efficacy prediction system described above.

Turning back to FIG. 5, the function of providing the efficacy prediction to the given individual may take other forms as well.

It should be understood that while the methods and examples above are generally described with respect to cannabinoid formulations, the methods can also be applied to other chemical compounds that may be used to treat a variety of health conditions.

IV. Conclusion

The present disclosure is not to be limited in terms of the particular embodiments described in this application, which are intended as illustrations of various aspects. Many modifications and variations can be made without departing from its scope, as will be apparent to those skilled in the art. Functionally equivalent methods and apparatuses within the scope of the disclosure, in addition to those described herein, will be apparent to those skilled in the art from the foregoing descriptions. Such modifications and variations are intended to fall within the scope of the appended claims.

The above detailed description describes various features and operations of the disclosed systems, devices, and methods with reference to the accompanying figures. The example embodiments described herein and in the figures are not meant to be limiting. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations.

With respect to any or all of the message flow diagrams, scenarios, and flow charts in the figures and as discussed herein, each step, block, and/or communication can represent a processing of information and/or a transmission of information in accordance with example embodiments. Alternative embodiments are included within the scope of these example embodiments. In these alternative embodiments, for example, operations described as steps, blocks, transmissions, communications, requests, responses, and/or messages can be executed out of order from that shown or discussed, including substantially concurrently or in reverse order, depending on the functionality involved. Further, more or fewer blocks and/or operations can be used with any of the message flow diagrams, scenarios, and flow charts discussed herein, and these message flow diagrams, scenarios, and flow charts can be combined with one another, in part or in whole.

A step or block that represents a processing of information can correspond to circuitry that can be configured to perform the specific logical functions of a herein-described method or technique. Alternatively or additionally, a step or block that represents a processing of information can correspond to a module, a segment, or a portion of program code (including related data). The program code can include one or more instructions executable by a processor for implementing specific logical operations or actions in the method or technique. The program code and/or related data can be stored on any type of computer readable medium such as a storage device including RAM, a disk drive, a solid state drive, or another storage medium.

The computer readable medium can also include non-transitory computer readable media such as computer readable media that store data for short periods of time like register memory and processor cache. The computer readable media can further include non-transitory computer readable media that store program code and/or data for longer periods of time. Thus, the computer readable media may include secondary or persistent long term storage, like ROM, optical or magnetic disks, solid state drives, compact-disc read only memory (CD-ROM), for example. The computer readable media can also be any other volatile or non-volatile storage systems. A computer readable medium can be considered a computer readable storage medium, for example, or a tangible storage device.

Moreover, a step or block that represents one or more information transmissions can correspond to information transmissions between software and/or hardware modules in the same physical device. However, other information transmissions can be between software modules and/or hardware modules in different physical devices.

The particular arrangements shown in the figures should not be viewed as limiting. It should be understood that other embodiments can include more or less of each element shown in a given figure. Further, some of the illustrated elements can be combined or omitted. Yet further, an example embodiment can include elements that are not illustrated in the figures.

While various aspects and embodiments have been disclosed herein, other aspects and embodiments will be apparent to those skilled in the art. The various aspects and embodiments disclosed herein are for purpose of illustration and are not intended to be limiting, with the true scope being indicated by the following claims.

What is claimed is:

1. A computer implemented method of treating a particular health condition for a user, wherein the method comprises:

prior to receiving a request to provide an efficacy prediction for a particular cannabinoid formulation to treat the particular health condition of the user, training a machine learning model, wherein training the machine learning model comprises:
identifying the particular health condition shared by a plurality of individuals;
receiving respective efficacy information indicating the efficacy of the particular cannabinoid formulation for treating the particular health condition share by the plurality of individuals;
receiving respective genetic information for each of the plurality of individuals; and
receiving respective biometric information for each of the plurality of individuals;
applying the machine learning model to group the plurality of individuals into a plurality of groups based on their (i) respective efficacy information; and (ii) similarities in their respective genetic information; and (iii) similarities in their respective biometric information;
based on receiving (i) the request to provide the efficacy prediction for the particular cannabinoid formulation to treat the particular health condition of the user; (ii) genetic information for the user; and (iii) biometric information for the user, applying the machine learning model to output:
the efficacy prediction for the particular cannabinoid formulation to treat the particular health condition of the user, wherein the efficacy prediction is based on the trained machine learning model and the genetic information and biometric information for the user; and an indication of whether the particular cannabinoid formulation was effective in treating the particular health condition for one or more groups of the plurality of groups based one or more similarities in their respective genetic and biometric information with the user;

receiving an updated indication of whether the particular cannabinoid formulation was effective in treating the particular health condition for the user; and retraining the machine learning model based on the updated indication.

2. The computer implemented method of claim 1, wherein the respective genetic information comprises a genome for each of the plurality of individuals, and wherein the genetic information for the user comprises a genome for the user.

3. The computer implemented method of claim 1, wherein the respective biometric information comprises one or more of (i) photoplethysmography data, (ii) oxygen saturation levels, (iii) arterial elasticity, (iv) peripheral elasticity, (v) sleep information, (vi) glucose levels, and (vii) blood pressure, and wherein the biometric information for the user comprises one or more of (i) photoplethysmography data, (ii) oxygen saturation levels, (iii) arterial elasticity, (iv) peripheral elasticity, (v) sleep information, (vi) glucose levels, and (vii) blood pressure.

4. The computer implemented method of claim 1, wherein receiving the respective biometric information comprises receiving at least a portion of the biometric information from a biometric device.

5. The computer implemented method of claim 1, wherein the machine learning model comprises a k-nearest neighbor machine learning technique.

6. The computer implemented method of claim 1, wherein the machine learning model comprises a k-means machine learning technique.

7. The computer implemented method of claim 1, further comprising:

reducing dimensionality of the respective genetic information prior to training the machine learning model.

8. The computer implemented method of claim 1, further comprising:

Reducing dimensionality of the respective biometric information prior to training the machine learning model.

9. The computer implemented method of claim 1, further comprising:

reducing dimensionality of the respective genetic information and the respective biometric information prior to training the machine learning model.

10. A computing system comprising:

at least one processor;

a non-transitory computer-readable medium; and program instructions stored on the non-transitory computer-readable medium that are executable by the at least one processor such that the computing system is capable of treating a particular health condition for a user via:

prior to receiving a request to provide an efficacy prediction for a particular cannabinoid formulation to treat the particular health condition of the user, training a machine learning model, wherein training the machine learning model comprises:

identifying the particular health condition shared by a plurality of individuals;

receiving respective efficacy information indicating the efficacy of the particular cannabinoid formulation for treating the particular health condition share by the plurality of individuals;

receiving respective genetic information for each of the plurality of individuals; and receiving respective biometric information for each of the plurality of individuals; and applying the machine learning model to group the plurality of individuals into a plurality of groups based on their (i) respective efficacy information; (ii) similarities in their respective genetic information; and (iii) similarities in their respective biometric information; and based on receiving (i) the request to provide the efficacy prediction for the particular cannabinoid formulation to treat the particular health condition of the user; (ii) genetic information for the user; and (iii) biometric information for the user, applying the machine learning model to output:

the efficacy prediction for the particular cannabinoid formulation to treat the particular health condition of the user, wherein the efficacy prediction is based on the trained machine learning model and the genetic information and biometric information for the user; and an indication of whether the particular cannabinoid formulation was effective in treating the particular health condition for one or more groups of the plurality of groups based one or more similarities in their respective genetic and biometric information with the user;

receiving an updated indication of whether the particular cannabinoid formulation was effective in treating the particular health condition for the user; and retraining the machine learning model based on the updated indication.

11. The computing system of claim 10, wherein the respective genetic information comprises a genome for each of the plurality of individuals, and wherein the genetic information for the user comprises a genome for the user.

12. The computing system of claim 10, wherein the respective biometric information comprises one or more of (i) photoplethysmography data, (ii) oxygen saturation levels, (iii) arterial elasticity, (iv) peripheral elasticity, (v) sleep information, (vi) glucose levels, and (vii) blood pressure, and wherein the biometric information for the user comprises one or more of (i) photoplethysmography data, (ii) oxygen saturation levels, (iii) arterial elasticity, (iv) peripheral elasticity, (v) sleep information, (vi) glucose levels, and (vii) blood pressure.

13. The computing system of claim 10, wherein the non-transitory computer-readable medium further comprises program instructions stored thereon that are executable by the at least one processor such that the computing system is capable of:

reducing dimensionality of the respective genetic information prior to training the machine learning model.

14. The computing system of claim 10, wherein the non-transitory computer-readable medium further comprises program instructions stored thereon that are executable by the at least one processor such that the computing system is capable of:

reducing dimensionality of the respective biometric information prior to training the machine learning model.

15. The computing system of claim 10, wherein the non-transitory computer-readable medium further comprises program instructions stored thereon that are executable by the at least one processor such that the computing system is capable of:

reducing dimensionality of the respective genetic information and the respective biometric information prior to training the machine learning model.

16. A non-transitory computer-readable medium comprising program instructions that are executable by at least one processor such that a computing system is capable of:

prior to receiving a request to provide an efficacy prediction for a particular cannabinoid formulation to treat a particular health condition of a user, training a machine learning model, wherein training the machine learning model comprises:

identifying the particular health condition shared by a plurality of individuals;

receiving respective efficacy information indicating the efficacy of the particular cannabinoid formulation for treating the particular health condition share by the plurality of individuals;

receiving respective genetic information for each of the plurality of individuals; and receiving respective biometric information for each of the plurality of individuals;

applying the machine learning model to group the plurality of individuals into a plurality of groups based on their (i) respective efficacy information; (ii) similarities in their respective genetic information; and (iii) similarities in their respective biometric information;

based on receiving (i) the request to provide the efficacy prediction for the particular cannabinoid formulation to treat the particular health condition of the user; (ii) genetic information for the user; and (iii) biometric information for the user, applying the machine learning model to output:

the efficacy prediction for the particular cannabinoid formulation to treat the particular health condition of the user, wherein the efficacy prediction is based on the trained machine learning model and the genetic information and biometric information for the user; and an indication of whether the particular cannabinoid formulation was effective in treating the particular health condition for one or more groups of the plurality of groups based one or more similarities in their respective genetic and biometric information with the user;

receiving an updated indication of whether the particular cannabinoid formulation was effective in treating the particular health condition for the user; and retraining the machine learning model based on the updated indication.

17. The non-transitory computer-readable medium of claim 16, wherein the non-transitory computer-readable medium further comprises program instructions stored thereon that are executable by the at least one processor such that the computing system is capable of:

reducing dimensionality of the respective genetic information and the respective biometric information prior to training the machine learning model.

18. The non-transitory computer-readable medium of claim 16, wherein the non-transitory computer-readable medium further comprises program instructions stored thereon that are executable by the at least one processor such that the computing system is capable of:

receiving an updated indication of whether the particular cannabinoid formulation was effective in treating the particular health condition for the user; and retraining the machine learning model based on the updated indication.

19. The non-transitory computer-readable medium of claim 16, wherein the respective genetic information comprises a genome for each of the plurality of individuals, and wherein the genetic information for the user comprises a genome for the user.

20. The non-transitory computer-readable medium of claim 16, wherein the respective biometric information comprises one or more of (i) photoplethysmography data, (ii) oxygen saturation levels, (iii) arterial elasticity, (iv) peripheral elasticity, (v) sleep information, (vi) glucose levels, and (vii) blood pressure, and wherein the biometric information for the user comprises one or more of (i) photoplethysmography data, (ii) oxygen saturation levels, (iii) arterial elasticity, (iv) peripheral elasticity, (v) sleep information, (vi) glucose levels, and (vii) blood pressure.

* * * * *